(12) United States Patent
Barbato

(10) Patent No.: US 6,444,970 B1
(45) Date of Patent: Sep. 3, 2002

(54) MINIATURE LOW-NOISE PHOTODIODE SYSTEM

(75) Inventor: Louis J. Barbato, Norwood, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/339,695

(22) Filed: Jun. 24, 1999

Related U.S. Application Data
(60) Provisional application No. 60/090,753, filed on Jun. 26, 1998.

(51) Int. Cl.[7] ............................................. H01J 40/14
(52) U.S. Cl. ................................... 250/214 A; 330/308
(58) Field of Search ..................... 250/214 A, 214 LA, 250/214 R, 214 AG, 214 C, 226; 330/308, 59, 291; 356/416, 417, 419; 606/2, 14, 15

(56) References Cited

U.S. PATENT DOCUMENTS

| | | | |
|---|---|---|---|
| 4,340,307 A | 7/1982 | Diamond et al. | 356/418 |
| 4,535,233 A | 8/1985 | Abraham | 250/214 A |
| 4,548,505 A | 10/1985 | Ono | 356/445 |
| 4,565,974 A | 1/1986 | Smoot | 330/304 |
| 4,623,786 A | 11/1986 | Rodwell | 250/214 A |
| 4,674,093 A | 6/1987 | Angerstein et al. | 372/38 |

(List continued on next page.)

FOREIGN PATENT DOCUMENTS

| | | | |
|---|---|---|---|
| EP | 0 314 937 A2 | 10/1989 | A61B/5/14 |
| EP | 0 650 694 A1 | 3/1995 | A61B/5/05 |
| EP | 0 792 618 A1 | 3/1997 | A61B/5/00 |
| EP | 0 920 831 A1 | 9/1999 | A61B/1/05 |
| WO | WO 97/01985 | 1/1997 | A61B/5/00 |
| WO | WO 98/22805 | 5/1998 | G01N/21/25 |

OTHER PUBLICATIONS

Ko. "Biomedical Sensors and Actuators," *Electronic Engineers' Handbook*, 3d ed., 1989, McGraw–Hill, Inc., pp. 26–53 to 26–68.

Meindl,"Implantable Telemetry in Biomedical Research," *Electronics Engineers' Handbook*, 3d ed., 1989, McGraw–Hill, Inc., pp. 26–41 to 26–53.

Gregory et al., "End to End Electro–Optical Modeling Software," *Optical Design and Analysis Software*, Jul. 21, 1999, SPIE, vol. 3780.

Optoelectronics Data Book, Advanced Photonix, Inc., Jul.21, 1999 or earlier, pp.6–7.

Microelectronics: Basic Amplifier Stages at Low Frequencies, 1987 pp. 444, 627, 628, 630.

Proelectron Electronic Schematics Web page http://www-.prolectron.net/elect/index.html downloaded Aug. 30, 1999.

National Semi Conductor Application Note 262, May 1981.

*Primary Examiner*—Kevin Pyo
(74) *Attorney, Agent, or Firm*—Testa, Hurwitz & Thibeault, LLP

(57) ABSTRACT

A miniature low-noise photodiode amplifier system that minimizes offset and drift has the output of a photodiode connected to the non-inverting input of an operational amplifier. The operational amplifier has a split voltage supply and the output of the operational amplifier is transmitted to a rectifying diode. A second amplifier to increase the output of the operational amplifier is not required when this miniature low-noise photodiode amplifier system is employed.

17 Claims, 7 Drawing Sheets

U.S. PATENT DOCUMENTS

| | | | |
|---|---|---|---|
| 4,750,216 A | 6/1988 | Boyce | 455/617 |
| 4,798,956 A * | 1/1989 | Hochstein | 250/349 |
| 4,803,992 A | 2/1989 | Lemelson | 128/634 |
| 4,850,043 A | 7/1989 | Winston | 455/607 |
| 4,882,482 A | 11/1989 | Smith et al. | 250/214 A |
| 4,882,623 A | 11/1989 | Uchikudo | 358/98 |
| 4,888,562 A | 12/1989 | Edler | 330/291 |
| 4,902,896 A | 2/1990 | Fertig, Sr. et al. | 290/348 |
| 4,928,172 A | 5/1990 | Uehara et al. | 358/98 |
| 4,930,516 A | 6/1990 | Alfano et al. | 128/665 |
| 4,938,602 A | 7/1990 | May et al. | 356/435 |
| 4,981,138 A | 1/1991 | Deckelbaum et al. | 128/665 |
| 5,001,556 A | 3/1991 | Nakamura et al. | 358/98 |
| 5,034,010 A | 7/1991 | Kittrell et al. | 606/15 |
| 5,056,503 A | 10/1991 | Nagasaki et al. | 128/6 |
| 5,073,700 A * | 12/1991 | D'Onofrio | 235/435 |
| 5,106,387 A | 4/1992 | Kittrell et al. | 606/15 |
| 5,116,759 A | 5/1992 | Klainer et al. | 435/288 |
| 5,125,404 A | 6/1992 | Kittrell et al. | 128/634 |
| 5,166,819 A | 11/1992 | Eichel | 359/189 |
| 5,187,572 A | 2/1993 | Nakamura et al. | 358/98 |
| 5,187,672 A | 2/1993 | Chance et al. | 364/550 |
| 5,198,658 A | 3/1993 | Rydin | 250/214 A |
| 5,206,174 A | 4/1993 | Gehrke et al. | 436/58 |
| 5,216,386 A | 6/1993 | Wyatt | 330/308 |
| 5,287,340 A | 2/1994 | Chapman et al. | 369/44.41 |
| 5,309,907 A | 5/1994 | Fang et al. | 128/633 |
| 5,345,073 A | 9/1994 | Chang et al. | 250/214 A |
| 5,351,532 A | 10/1994 | Hager | 73/153 |
| 5,382,920 A | 1/1995 | Jung | 330/308 |
| 5,467,767 A | 11/1995 | Alfano et al. | 128/665 |
| 5,477,370 A | 12/1995 | Little et al. | 359/189 |
| 5,512,757 A | 4/1996 | Cederstrand et al. | 250/373 |
| 5,515,392 A | 5/1996 | Teremy | 372/38 |
| 5,545,897 A | 8/1996 | Jack | 250/339.13 |
| 5,553,614 A | 9/1996 | Chance | 128/633 |
| 5,556,421 A | 9/1996 | Prutchi et al. | 607/36 |
| 5,592,124 A | 1/1997 | Mullins | 330/308 |
| 5,610,709 A | 3/1997 | Arrington et al. | 356/218 |
| 5,646,573 A | 7/1997 | Bayruns et al. | 330/59 |
| 5,647,368 A | 7/1997 | Zeng et al. | 128/665 |
| 5,696,657 A | 12/1997 | Nourrcier, Jr. et al. | 361/93 |
| 5,714,909 A | 2/1998 | Jackson | 330/308 |
| 5,767,538 A | 6/1998 | Mullins et al. | 257/115 |
| 5,801,588 A | 9/1998 | Nishiyama | 330/308 |
| 5,875,050 A | 2/1999 | Ota | 359/189 |

* cited by examiner

_US 6,444,970 B1_

MINIATURE LOW-NOISE PHOTODIODE SYSTEM

CROSS-REFERENCE TO RELATED APPLICATION

This is based on, and claims the benefit of and priority to, U.S. provisional patent application Ser. No. 60/090,753 filed on Jun. 26, 1998.

TECHNICAL FIELD

The invention relates to light amplification and, more particularly, to amplification of an output of a photodiode.

BACKGROUND INFORMATION

Spectral analysis of living tissue can be used to detect various forms of cancer and other types of diseases. In spectral analysis, light illuminates tissue region under examination and a light detector detects optical properties of the illuminated tissue region by measuring light energy modified by its interaction with the tissue region in a pre-determined frequency and amplitude domain. Optical properties include absorption, luminescence, fluorescence, frequency and time-domain responses to various materials injected to the tissue region and other electromagnetic responses. Diseased tissue may be identified by comparing a spectrum obtained to spectra of normal tissue obtained under the same controlled conditions.

Current devices available for tissue characterization using spectral analysis include night vision sensing systems with filtering adapted to be used with endoscopes and multichannel fiber optic delivery systems. The latter systems typically include a light source, a first optical conduit, a light applicator and receiver, a second optical conduit, a spectrometer and a display unit. The receiver used to receive the reflective light can be a photodiode. A photodiode amplifier can be used to amplify the output from the photodiode.

Photodiode amplifiers are typically used in conjunction with an operational amplifier circuit. An output of a photodiode can be amplified in a photoconductive mode illustrated in FIG. 1. In the photoconductive mode, an amplifier circuit 100 includes a photodiode 110, an operational amplifier (Op-Amp) 115, and a feedback resistor 130. A cathode 110a of the photodiode 110 is coupled to an inverting input 115a of the operational amplifier 115 via a resistor 120. An anode 110b of the photodiode 110 is coupled to a voltage source 140. A non-inverting input 115b of the operational amplifier 115 is coupled to ground 125. An output 115c of the operational amplifier 115 is fed back to the inverting input 115a through the feedback resistor 130. A capacitor 135 is connected in parallel with the feedback resistor 130 to filter out unwanted noise.

Alternatively, an output of the photodiode 110 can be amplified in a photovoltaic mode as illustrated in FIG. 2. The only difference between the photoconductive mode and the photovoltaic mode is the manner in which the photodiode is connected to the operational amplifier. In the photovoltaic mode, the cathode 110a' of the photodiode 110' is coupled to the inverting input 115a' of the operational amplifier 115' and the anode 110b' of the photodiode 110' is connected to the non-inverting input 115b' of the operational amplifier 115'.

In both the photoconductive and the photovoltaic modes, a current output from the photodiode 110, 110' is applied to the operational amplifier 115, 115'. The operational amplifier 115, 115' provides a voltage output equal to the value of the resistance of the feedback resistor 130, 130' multiplied by the current from the photodiode 110, 110' which passes through the feedback resistor 130, 130'. In an "ideal" situation, the gain of this system is directly related to the feedback resistor 130, 130' based on the following equation:

$$V_{OUT} = I_L R_f$$

Such an ideal situation is fictional and is rarely realized in practice as other components must be added to compensate for offset currents and voltage drift. These components tend to decrease the gain of the system. Since the gain is decreased and the output is negative, a second amplifier needs to be coupled to the first amplifier in order to provide a positive output voltage with moderate gain. Compensation still takes place with the second amplifier, and this system will still tend to drift slightly. The outcome is a larger system that is not very sensitive and which usually requires re-calibration steps, alignment or other compensatory actions, and is more costly because of the number of components, and the complexity of manufacture.

SUMMARY OF THE INVENTION

In one aspect, the invention features an amplifier circuit. The amplifier circuit includes an operational amplifier, a light-sensitive device, a feedback module, and a rectifier. The operational amplifier includes an inverting input, a non-inverting input, and an output. The light-sensitive device is in electrical communication with the non-inverting input of the operational amplifier. The feedback module is in electrical communication with the output of the operational amplifier and the inverting input of the operational amplifier. The rectifier is in electrical communication with the output of the operational amplifier.

In one embodiment according to this aspect of the invention, the rectifier is a rectifying diode. In another embodiment, the light-sensitive device is a photodiode. In another embodiment, the feedback module includes a resistor. In one detailed embodiment, the feedback module further includes a capacitor. In another embodiment, the amplifier circuit further includes a resistance in electrical communication with the inverting input of the operational amplifier. In still another embodiment, the amplifier circuit further includes a resistance in electrical communication with the rectifier.

In another aspect, the invention involves a spectrometer comprising an amplification circuit, a light source for illuminating tissue, and a light-sensitive device. The amplifier circuit includes an operational amplifier, a feedback module, and a rectifier. The operational amplifier includes an inverting input, a non-inverting input, and an output. The feedback module is in electrical communication with the output of the operational amplifier and the inverting input of the operational amplifier. The rectifier is in electrical communication with the output of the operational amplifier. The light-sensitive device is in electrical communication with the non-inverting input of the operational amplifier. The light-sensitive device detects optical properties of the illuminated tissue.

In one embodiment of this aspect of the invention, the light source is internal to the spectrometer. In another embodiment, the light source is external to the spectrometer. In one embodiment, the amplifier circuit comprises a plurality of operational amplifiers. In another embodiment, the spectrometer further comprises a light filter disposed between the illuminated tissue and the light-sensitive device. In one detailed embodiment, the spectrometer further comprises a second light-sensitive device and a second light filter disposed between the illuminated tissue and the light-sensitive device. In another detailed embodiment, the first light filter passes through a first range of wavelengths of light and the second light filter passes through a second wavelengths of light.

In still another aspect, the invention relates to a method for amplifying an output of a photodiode. According to the method, an amplifier circuit comprising a light-sensitive device, a rectifier, and an operational amplifier with an inverting input, a non-inverting input, and a output is provided. A first voltage is applied to the inverting input of the operational amplifier. An optical signal is detected through the light-sensitive device which converts the optical signal to a second voltage. The second voltage is applied to a non-inverting input of the operational amplifier, wherein the first voltage and second voltage have opposite polarity. The output generated by the operational amplifier is transmitted to the rectifier, and an output with the same polarity as the second voltage is transmitted through the rectifier.

In one embodiment according to this aspect of the invention, the method further includes the step of stabilizing the output transmitted through the rectifier. In another embodiment, the first voltage from the output of the operational amplifier is applied to the inverting input of the operational amplifier. In still another embodiment, the method further comprises filtering noise in connection with the optical signal.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 1:
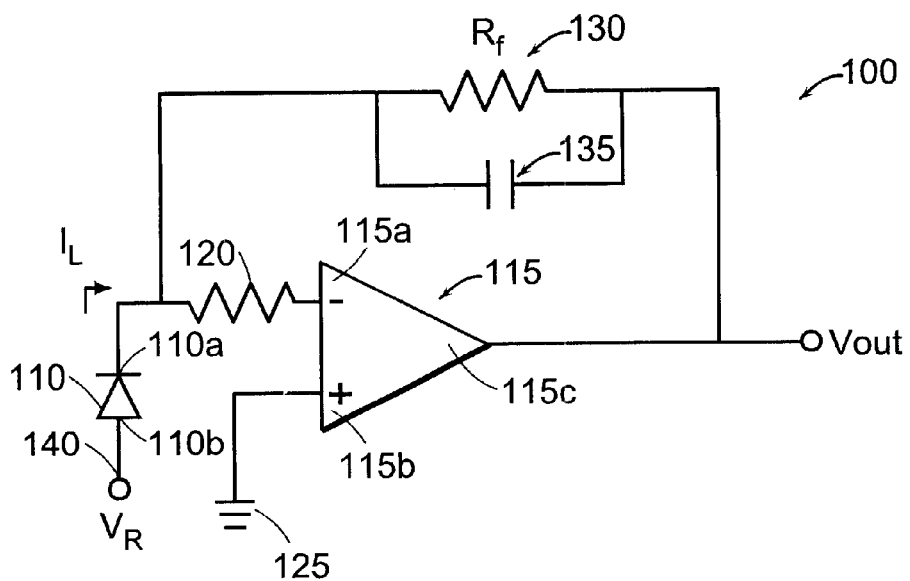
FIG. 1 shows an amplifier circuit.
Figure 2:
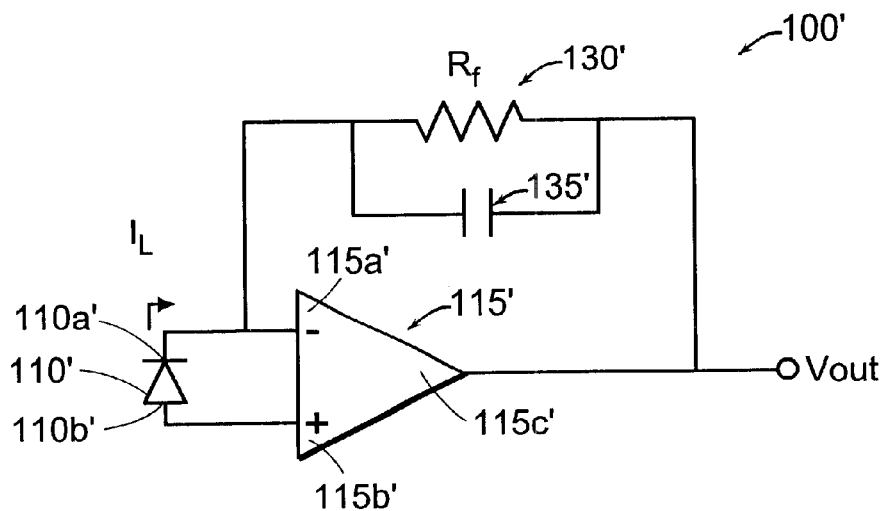
FIG. 2 shows another amplifier circuit.
Figure 3:
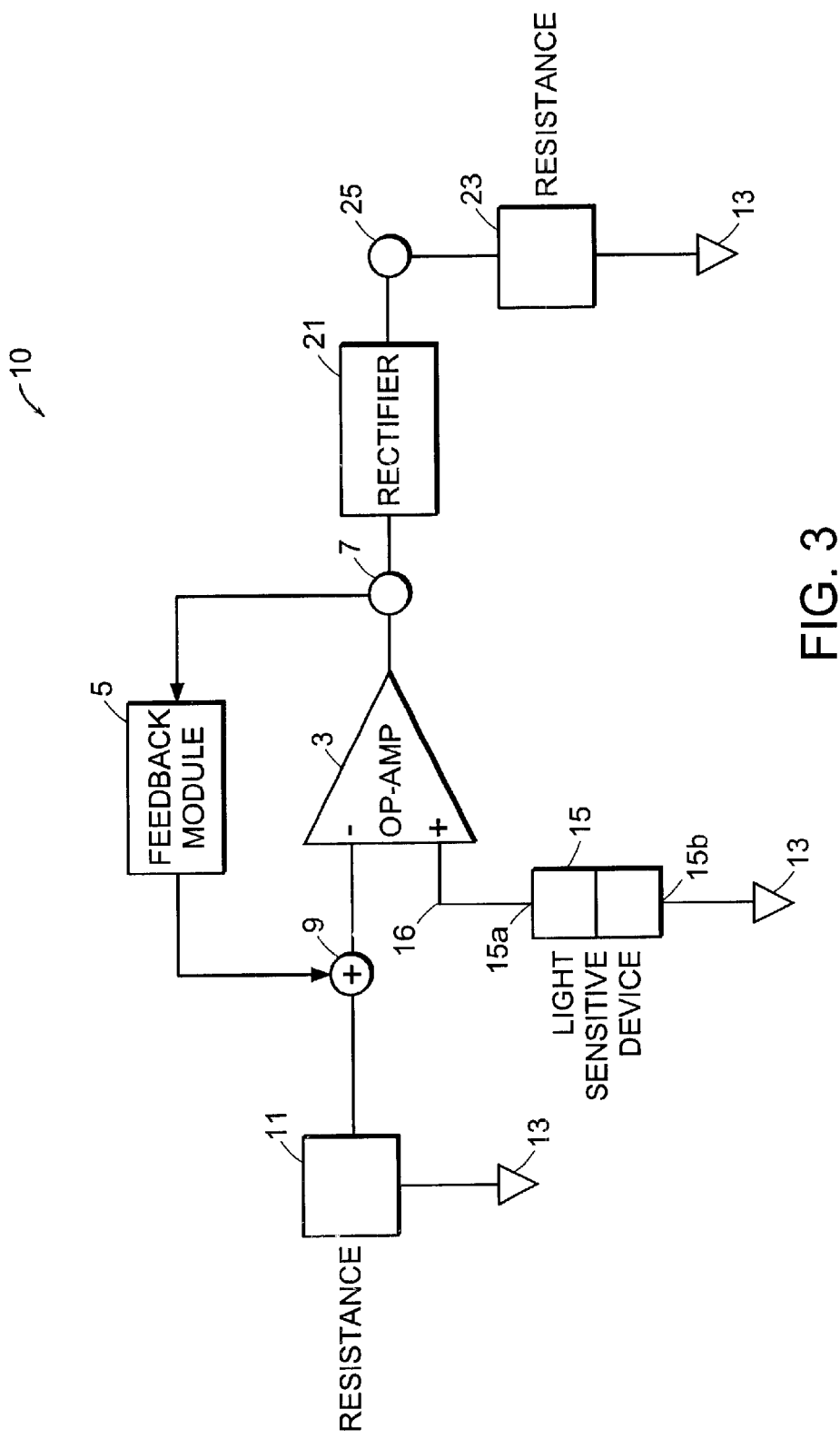
FIG. 3 shows an amplifier circuit in accordance with the invention.

Referring to FIG. 3, an amplifier circuit 10 includes a photodiode 15, an operational amplifier 3, a feedback module 5, a first resistor 11, a rectifier 21, and a second resistor 23. The photodiode 15 has its anode 15a coupled to a non-inverting input 16 of the operational amplifier 3 and its cathode 15b connected to ground 13. The inverting input 9 of the operational amplifier 3 is connected to ground 13 through the resistor 11. The output 7 of the operational amplifier 3 is coupled to the feedback module 5 and the rectifier 21. The feedback module 5 is coupled to the inverting input 9 of the operational amplifier 3. In one embodiment, the feedback module 5 includes a resistor. In another embodiment, the feedback module 5 includes a resistor and a capacitor. When light is not applied to the photodiode 15, the offset currents will force the output 7 of the operational amplifier 3 to reach the maximum negative supply voltage. The operational amplifier 3 will remain at the maximum negative supply voltage until light is applied to the photodiode 15. When light is applied to the photodiode 15, a positive voltage is applied to the non-inverting input 16 of the operational amplifier 3. By splitting the voltage to the operational amplifier 3 by applying the operational amplifier output 7 to the inverting input 9 of the operational amplifier 3 and by applying voltage from the photodiode 15 to the non-inverting input 16 of the operational amplifier, a split voltage is applied to the operational amplifier 3.

The rectifier 21 allows current to flow in only one direction. In one embodiment, the rectifier 21 is a rectifying diode. When no light is applied to the photodiode 15, the rectifier 21 becomes reverse biased, and no current can flow to the output 25. A voltage reading at this point would now be zero. When light is applied to the photodiode 15, the operational amplifier output 7 swings positive, forward biases the rectifier diode 21, and allows current to flow to the output 25. The voltage present at the output 25 is dependent on the amount of light reaching the photodiode 15. For added stability, a load resistor 23 can coupled to the rectifier 21 in one direction and ground 13 in the other direction.

Figure 4:
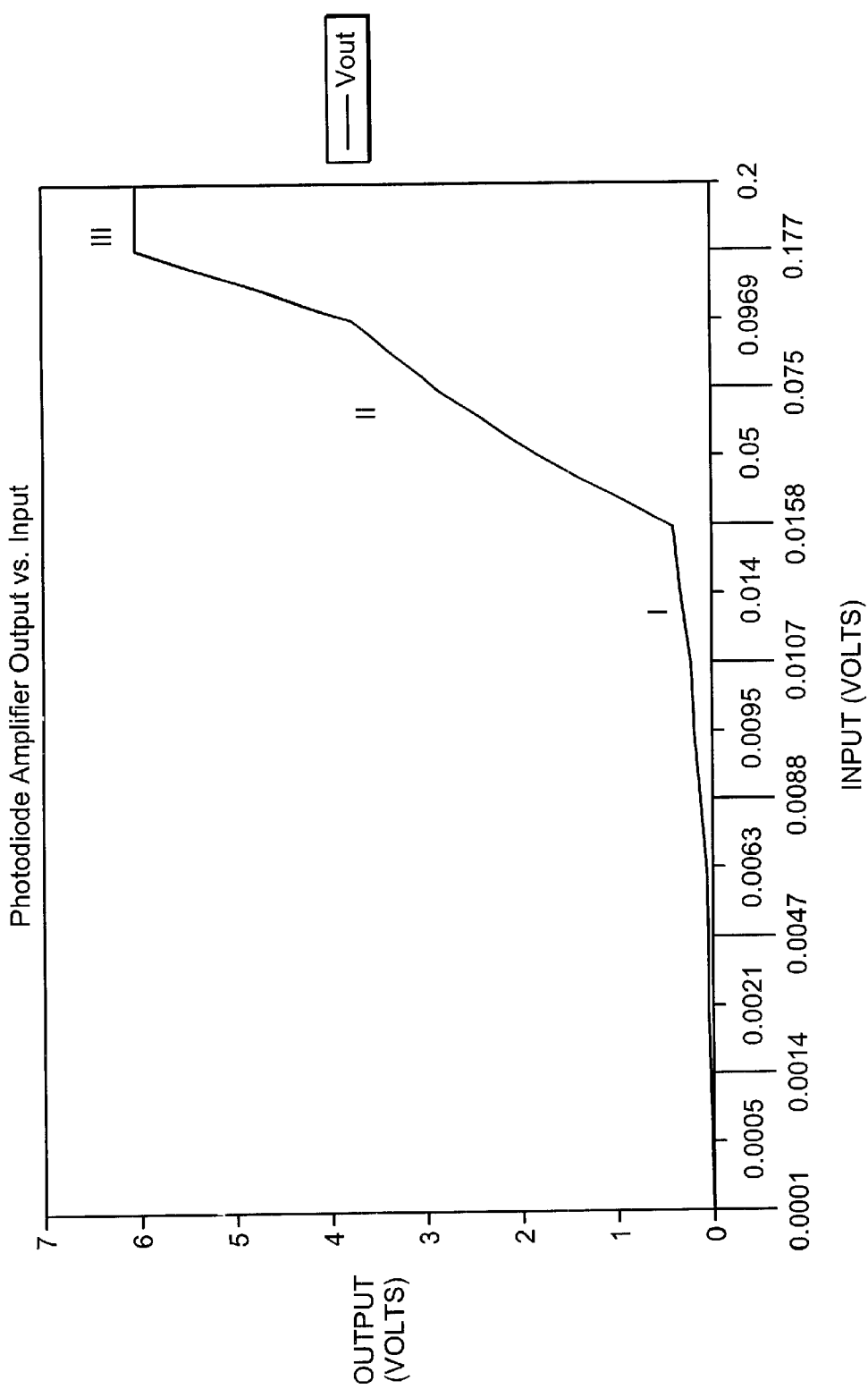
FIG. 4 shows a curve of photodiode amplifier output vs. input

FIG. 4 shows a graph of an output voltage of the amplifier circuit of FIG. 3 as a function of the input voltage applied to the operational amplifier of the circuit. FIG. 4 illustrates that the output voltage is always positive. The output voltage remains low in the threshold region (I) where the input voltage is between about 0.0001 volts and 0.0158 volts. Once the input voltages are in the range between 0.0158 and 0.177 volts the output is now in the operable region (II). Once the input voltage is above 0.177 volts (III), the output is in the saturation region (III). The sensitive voltage range is determined by the values of the first resistor 11 and the resistor in the feedback module 5. At 0.177 input volts this circuit reaches its saturation level.

Figure 5:
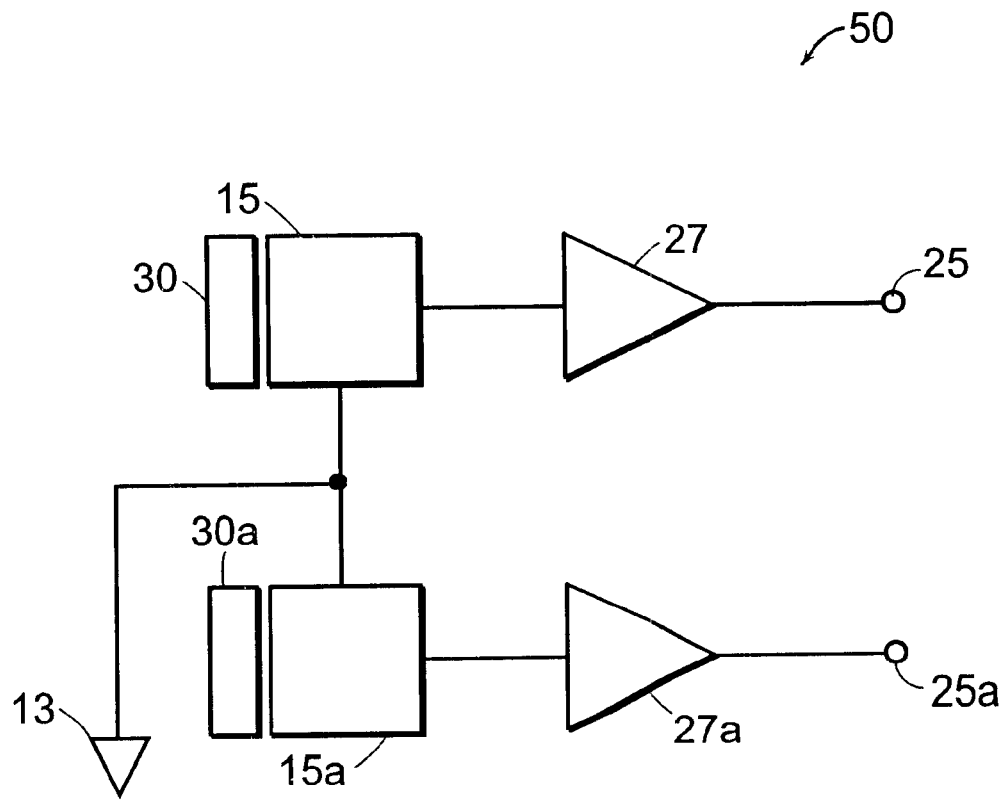
FIG. 5 is a block diagram of a spectrometer according to the invention.

Referring now to FIG. 5, an amplifier circuit 50 includes a first photodiode 15, a second photodiode 15A, a first operational amplifier 27, a second operational amplifier 27A, a first light filter 30 and a second light filter 30a. The first light filter 30 is positioned in the optical pathway of light to the first photodiode 15. The first light filter 30 transmits light having a wavelength within a first range of wavelengths. The second light filter 30a is positioned in the optical pathway of light to the second photodiode 15A. The second light filter 30 transmits light having a wavelength within a second range of wavelengths. The first photodiode 15 is coupled to the first operational amplifier 27. The second photodiode 15A is coupled to the second operational amplifier 27A. Both photodiodes 15 and 15A are connected to ground 13. The voltage outputs of the system are 25 and 25A.

Figure 6:
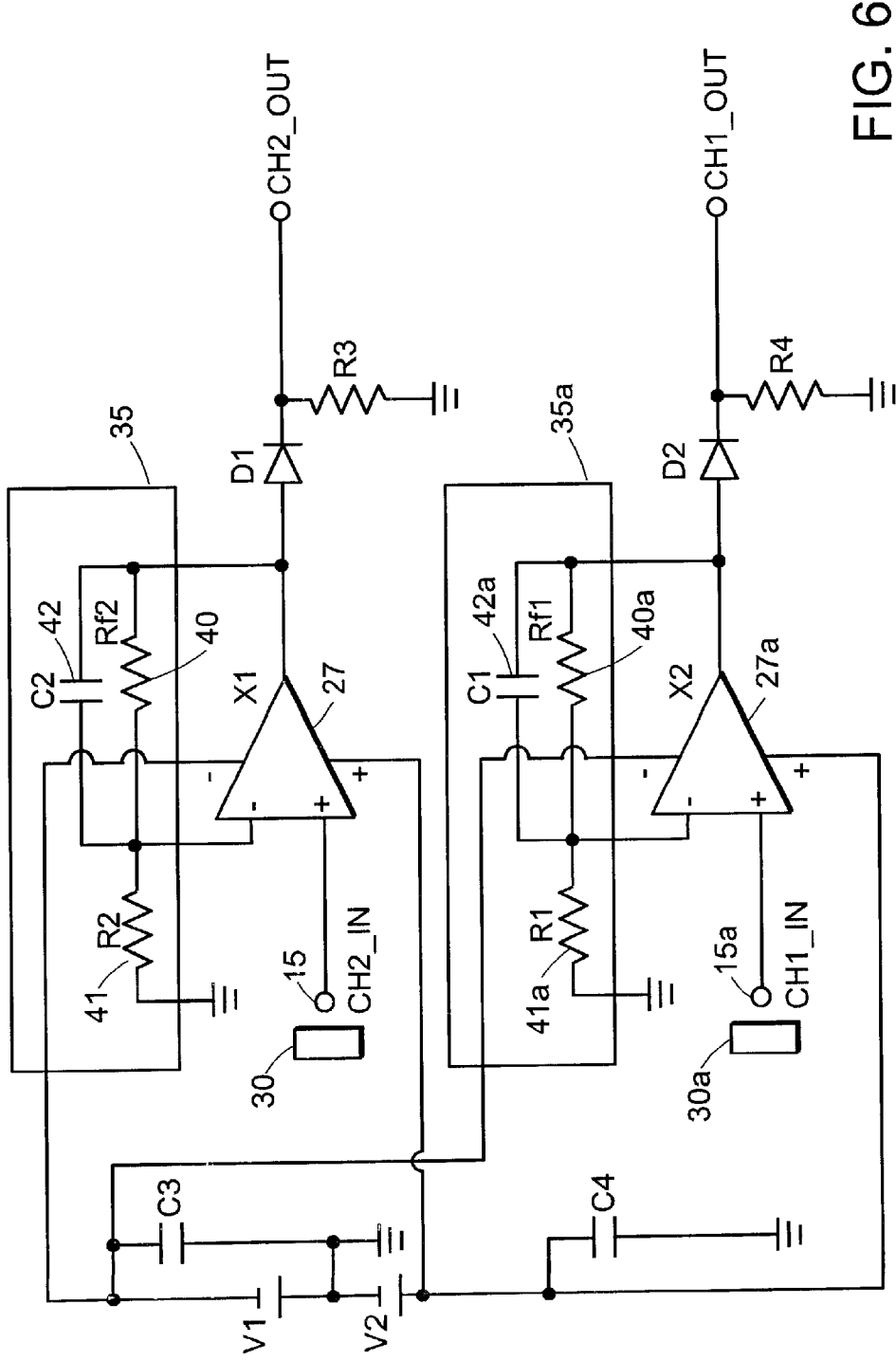
FIG. 6 is a schematic diagram of the spectrometer.

FIG. 6 shows a detailed circuit diagram of the amplifier circuitry of FIG. 5. Photodiodes 15 and 15a are in electrical communication with operational amplifiers 27 and 27a respectively. The photodiodes 15 and 15a are filtered by respective filters 30 and 30a. For this particular system, the two photodiodes 30 and 30a can be filtered to pass 440 nm in filter 30 and 370 nm light respectively. The output of each amplifier is fed into respective feedback modules 35 and 35a. Feedback module 35 is comprised of two series resistors 40 and 41 in parallel with a capacitor 42. Feedback module 35a is also comprised of two series resistors 40a and 41a in parallel with a capacitor 42a.

Figure 7:
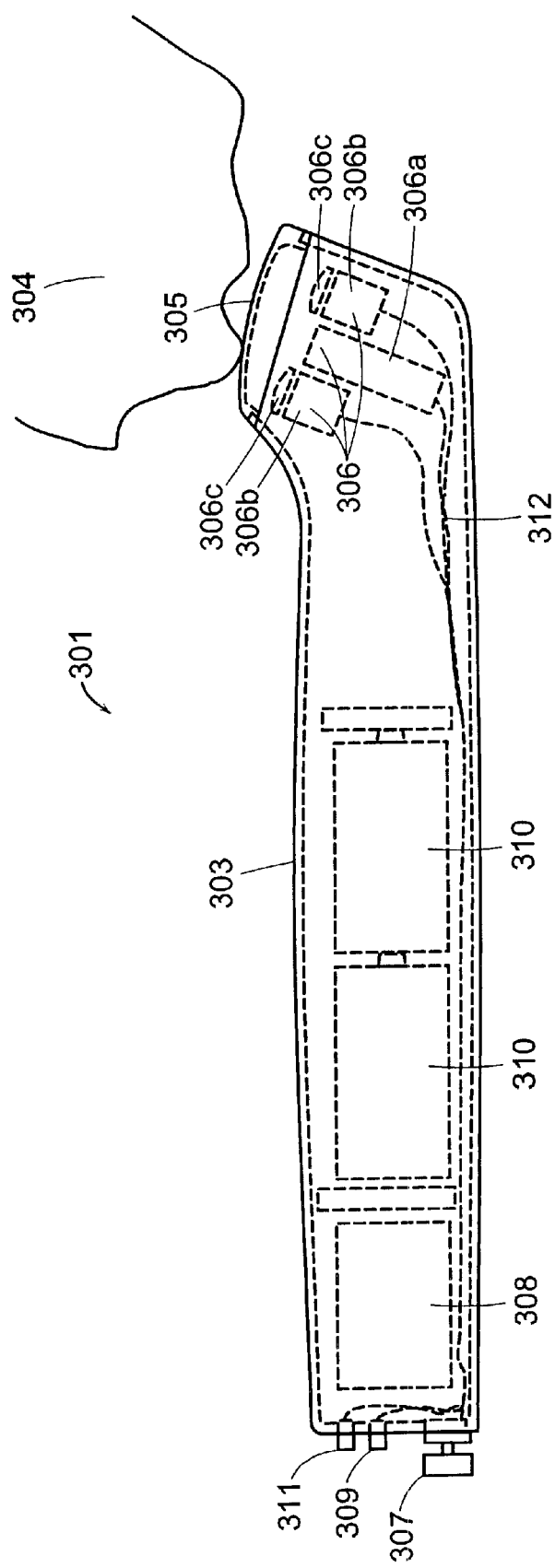
FIG. 7 shows a spectroscopy probe according to the invention.

Referring to FIG. 7, a tissue spectroscopy probe 301 includes a spectroscopic component module 306, a power source 310, and a control module 308 disposed inside a housing 303. The spectroscopic component module 306 includes a light source 306a and light detectors 306b. The light source 306a illuminates the tissue 304, and the detectors 306b detect spectroscopic properties of the illuminated tissue 304. The light source 306a can be, for example, a laser or a diode capable of emitting light at a pre-determined wavelength. Light filters 306c can be disposed between the detectors 306b and the illuminated tissue 304 to allow light of a predetermined wavelength to pass through to the detectors 306b. The spectroscopic component module 306 may comprise one or more light sources 306a and one or more light detectors 306b. The light source 306a and the light detectors 306b are electrically coupled to the power source 310 through cables 312.

The housing 303 includes a distal window 305, and the spectroscopic component module 306 is disposed adjacent the window 305. The probe 301 further includes a proximally mounted actuation switch 307, and indicators 309 and 311. In one embodiment, the indicator 309 is a red light, which is actuated to indicate cancerous tissue, and the indicator 311 is a green light, which is actuated to indicate normal tissue. The probe 301 is sized and shaped to fit inside a body cavity, which provides access to a tissue 304 to be examined, while the proximal end of the probe 301 remains outside the body for manipulation and control as well as for allowing the operator to observe the indicators 309, 311.

The power source 310 is electrically coupled to the control module 308. In one embodiment, the power source 310 includes a plurality of batteries, which provide DC power to the light source 306a, the light detectors 306b, the control module 308 and the indicators 309, 311. The control module 308 performs a variety of functions including: regulating the power delivered to the light source 306a; converting the detected light from an analog to a digital signal; and providing the logical function and display driver to the indicators 309 and 311. The light detectors 306b, the indicators 309, 311 and the control module 308, as used as a display driver for the indicators 309, 311, can be implemented by utilizing the circuit as described in FIG. 5 and FIG. 6.

The probe 301 may be tapered, cylindrical or elongated in shape. The housing 303 may be constructed of a flexible material such as vinyl or polyethylene. The flexible housing 303 permits the probe 301 to be inserted inside the body cavity with greater comfort. Other materials suitable to form the housing 303 include plastics, metals or composites such as carbon fiber or glass fiber composites that exhibit low thermal conductivity. In one embodiment, the housing 303 is constructed of a material having a low thermal conductivity. Low thermal conductivity of the housing material prevents the person from feeling the coldness of the metal instruments disposed inside the housing 303 and prevents any heat that may be generated from the internal electronics from propagating out of the housing 303.

Figure 8:
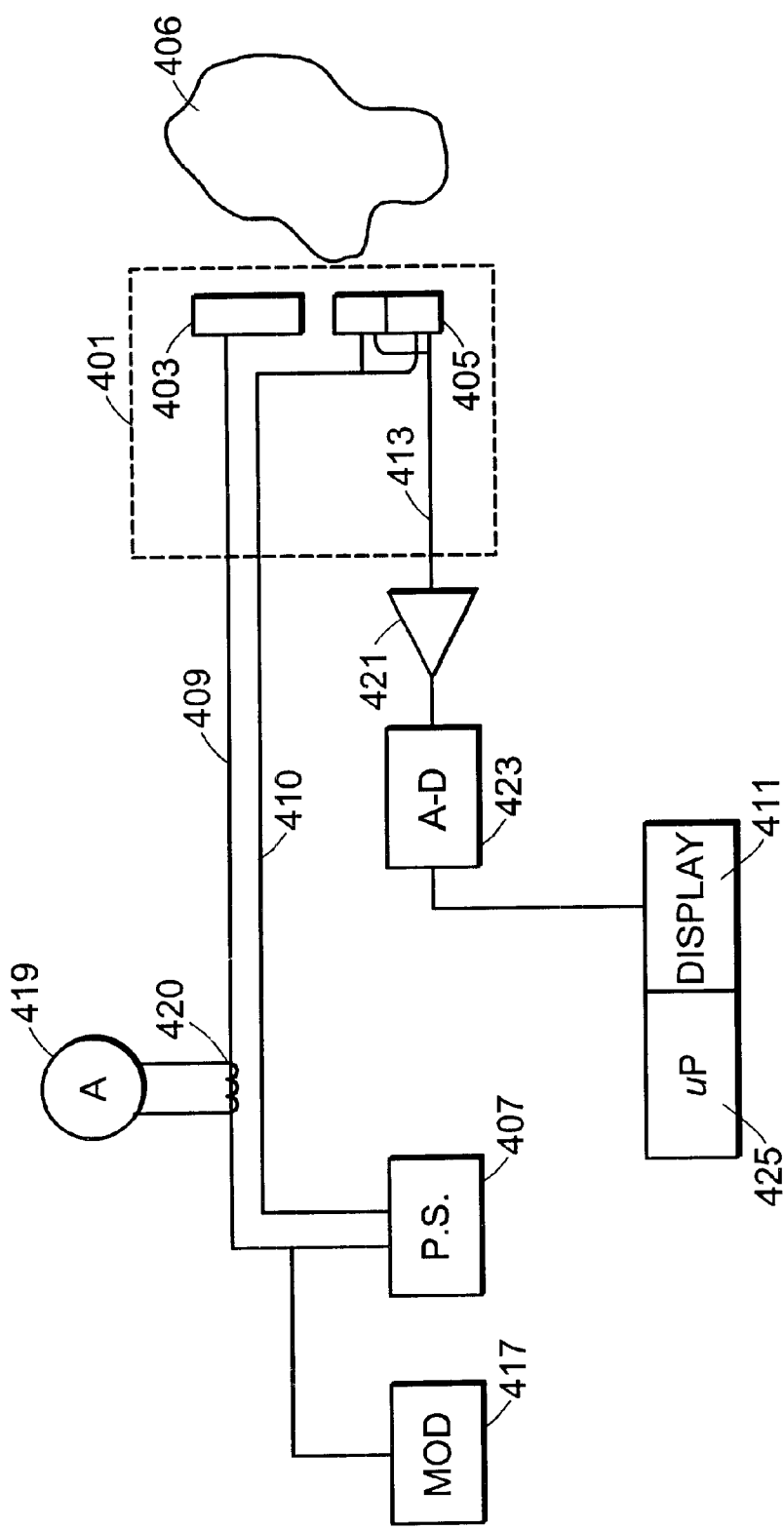
FIG. 8 is a block diagram of a system for spectral analysis including a spectrometer module in communication with external components.

The tissue spectroscopy probe 301 is an embodiment of the circuit illustrated in FIG. 8. Referring to FIG. 8, the spectrometer module 401 includes a light source 403 and a multi-channel light detector 405 in close proximity to each other and to a region of interest 406. The region of interest 406 may be living tissue located inside a body. The light source 403 and the light detector 405 are located in close proximity to the region of interest so that they may both emit and/or couple the light energy efficiently with minimum intervening space or material. The light source 403 is in communication with a power supply or source 407 through a DC power line 409, and the light detector 405 is in communication with the power source 407 through a bias supply line 410. The light source 403 may be internal or external to the module 401. The power source 407 may provide direct current (DC) of either high or low voltage, alternating current (AC) of an appropriate frequency, or a pulse. AC power may be supplied to the light source 403 for the purpose of modulating the light source with a modulator 417. Alternatively, current with complex waveforms may be supplied to the light source 403. A diode may be placed in the circuit at the light source 403 to rectify some of the AC power so that it can be used to bias the detector 405. In the disclosed embodiment, a metering device 419 is placed at the source of power and employs a current sampler 420 in line to monitor and display the power applied to the light source 403. This configuration may be used to help calibrate the instrument during use.

One or more output lines 413 extend from the detector 405 to a microprocessor 425 and a display 411 through an amplifier 421 and an A–D converter 423. The output lines 413 may be shielded to reduce noise pickup. The output of the detector 405 is amplified through an amplifier 421 and sent to an analog-to-digital (A–D, A/D, or A-to-D) converter 423. The digitized signal can then be sent to a microprocessor 425 or other logical device for subsequent spectral analysis.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. An amplifier circuit, comprising:
   an operational amplifier, including an inverting input, a non-inverting input, and an output;
   a light-sensitive device comprising a first terminal and a second terminal, the first terminal in electrical communication with the non-inverting input of the operational amplifier and the second terminal connected to ground;
   a feedback module in electrical communication with the output of the operational amplifier and the inverting input of the operational amplifier; and
   a rectifier in electrical communication with the output of the operational amplifier.

2. The amplifier circuit of claim 1 wherein the rectifier comprises a rectifying diode.

3. The amplifier circuit of claim 1 further comprising a resistance in electrical communication with the inverting input of the operational amplifier.

4. The amplifier circuit of claim 1 further comprising a resistance in electrical communication with the rectifier.

5. The amplifier circuit of claim 1 wherein the feedback module includes a resistor.

6. The amplifier circuit of claim 5 wherein the feedback module further includes a capacitor.

7. The amplifier circuit of claim 1 wherein the light-sensitive device comprises a photodiode.

8. A spectroscopy probe, comprising:
   an amplifier circuit comprising an operational amplifier, a feedback module and a rectifier;

the operational amplifier comprises an inverting input, a non-inverting input, and an output;

the feedback module is in electrical communication with the output of the operational amplifier and the inverting input of the operational amplifier; and the rectifier is in electrical communication with the output of the operational amplifier;

a light source for illuminating tissue; and a light-sensitive device comprising a first terminal and a second terminal, the first terminal in electrical communication with the non-inverting input of the operational amplifier and the second terminal connected to ground, wherein the light-sensitive device detects optical properties of the illuminated tissue.

9. The spectroscopy probe of claim 8 wherein the light source is internal to the spectroscopy probe.

10. The spectroscopy probe of claim 8 wherein the amplifier circuit comprises a plurality of operational amplifiers.

11. The spectroscopy probe of claim 8 further comprising a light filter disposed between the illuminated tissue and the light-sensitive device.

12. The spectroscopy probe of claim 11 further comprising a second light-sensitive device and a second light filter disposed between the illuminated tissue and the second light-sensitive device.

13. The spectroscopy probe of claim 12 wherein the first light filter passes through a first range of wavelengths of light and the second light filter passes through a second range of wavelengths of light.

14. A method for amplifying an output of a light-sensitive device comprising:

a) providing an amplifier circuit comprising the light-sensitive device, an operational amplifier, and a rectifier, wherein a non-inverting input of the operational amplifier is in electrical communication with a first terminal of the light-sensitive device and a second terminal of the light-sensitive device is connected to ground;

b) applying a first voltage to an inverting input of the operational amplifier;

c) detecting an optical signal through the light-sensitive device, wherein the light-sensitive device converts the optical signal to a second voltage;

d) applying the second voltage to the non-inverting input of the operational amplifier, wherein the first voltage and the second voltage have opposite polarity;

e) applying an output generated by the operational amplifier to the rectifier; and f) transmitting the output having a polarity of the second voltage through the rectifier.

15. The method of claim 14 further comprising the step of stabilizing the output transmitted through the rectifier.

16. The method of claim 14 wherein step b comprises applying the first voltage from the output of the operational amplifier to the inverting input of the operational amplifier.

17. The method of claim 14 further comprising filtering noise in connection with the optical signal.

* * * * *